(12) United States Patent
Sikdar et al.

(10) Patent No.: US 9,931,230 B2
(45) Date of Patent: Apr. 3, 2018

(54) ARTIFICIAL BODY PART CONTROL SYSTEM USING ULTRASONIC IMAGING

(75) Inventors: Siddhartha Sikdar, Washington, DC (US); Joseph J. Pancrazio, Boyds, MD (US); Ira A. Hunt, McLean, VA (US); Andrew J. Nelson, Burke, VA (US); Abdullah Al-Imran, Herndon, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 664 days.

(21) Appl. No.: 13/564,084

(22) Filed: Aug. 1, 2012

(65) Prior Publication Data
US 2013/0041477 A1 Feb. 14, 2013

Related U.S. Application Data

(60) Provisional application No. 61/513,789, filed on Aug. 1, 2011.

(51) Int. Cl.
| | | |
|---|---|---|
| *A61B 8/00* | (2006.01) | |
| *A61F 2/72* | (2006.01) | |
| *A61B 8/08* | (2006.01) | |
| *A61F 2/58* | (2006.01) | |
| *A61B 5/11* | (2006.01) | |
| *A61F 2/76* | (2006.01) | |
| *A61F 2/68* | (2006.01) | |

(52) U.S. Cl.
CPC .............. *A61F 2/72* (2013.01); *A61B 5/1107* (2013.01); *A61B 8/085* (2013.01); *A61B 8/4227* (2013.01); *A61B 8/5223* (2013.01); *A61F 2/583* (2013.01); *A61F 2002/6809* (2013.01); *A61F 2002/7615* (2013.01)

(58) Field of Classification Search
None
See application file for complete search history.

(56) References Cited

U.S. PATENT DOCUMENTS

| 5,818,359 | A | * | 10/1998 | Beach | G06F 3/011 340/4.11 |
|---|---|---|---|---|---|
| 5,840,047 | A | | 11/1998 | Stedham | |
| 6,053,869 | A | | 4/2000 | Kawagishi | |
| 6,298,269 | B1 | * | 10/2001 | Sweeney | 607/28 |
| 6,704,600 | B2 | * | 3/2004 | Daum | 607/30 |

(Continued)

FOREIGN PATENT DOCUMENTS

| CA | 2332747 | | 4/2001 | |
|---|---|---|---|---|
| EP | 0 865 262 | | 1/2002 | |
| WO | WO 97/15249 | * | 5/1997 | ............... A61F 2/68 |

OTHER PUBLICATIONS

Y.P. Zheng, M.M.F. Chan, J. Shi, X. Chen, Q.H. Huang, Sonomyography: Monitoring morphological changes of forearm muscles in actions with the feasibility for the control of powered prosthesis. Jul. 2005, Medical Engineering and Physics, vol. 28, pp. 405-415.*

(Continued)

*Primary Examiner* — James Kish
(74) *Attorney, Agent, or Firm* — Ballard Spahr LLP

(57) ABSTRACT

The artificial body part control system using ultrasonic imaging includes of an ultrasonic transducer coupled with an ultrasonic image analyzer which may be adapted to transmit a control signal to an artificial body part.

25 Claims, 9 Drawing Sheets

(56) References Cited

U.S. PATENT DOCUMENTS 6,984,208 B2* 1/2006 Zheng .......................... 600/438
8,046,058 B2 10/2011 Lin

OTHER PUBLICATIONS

Stegman et al., "Doppler ultrasound-based measurement of tendon velocity and displacement for application toward detecting user-intended motion." Jounral of Engineering in Medicine; (2012) 226(7). pp. 536-547.*

Korstanje et al., "Development and validation of ultrasound speckle tracking to quantify tendon displacement." Journal of Biomechanics; 43 (2010). pp. 1373-1379.*

Shi et al., "Feasibility of controlling prosthetic hand using sonomyography signal in real time: Preliminary study", Journal of Rehabilitation Research and Development, vol. 47, No. 2, 2010, p. 87-98.

Douglas et al., "Ultrasonic Imaging in Lower Limb Prosthetics", IEEE Transactions on Neural Systems and Rehabilitation Engineering, vol. 10, No. 1, Mar. 2002, p. 11-21.

Stegman, Kelly et al., "Doppler ultrasound-based measurement of tendon velocity and displacement for application toward detecting user-intended motion", Proceedings of the Institution of Mechanical Engineers, Part H: Journal of Engineering in Medicine, May 15, 2012. p. 536-547.

Shi, Jun et al., "A Pilot Study of the SMG Controlled Prosthesis", IEEE/ICME International Conference on Complex Medical Engineering, 2007, p. 1190-1193.

Rolock, Joshua S. PhD et al., "Amputations and Limb Prostheses", www.rehab.reseach.va.gov/prog/97/97prch01.htm, p. 1-30, May 26, 1999.

Krouskop, t et al., "A pulsed Doppler ultrasonic system for making noninvasive measrements of the mechanical properties of soft tissue", Journal of Rehabilitation Research and Development, vol. 24, No. 2, p. 1-8, Spring 1987.

Guo, Jing-Yi et al., "Comparison of Sonomyography and Electromyography of Forearm Muscles in the Guided Wrist Extension", Proceeding of the 5th International Workshop on Wearable and Implantable Body Sensor Networks, in conjunction with the 5th International Summer School and Symposium on Medical Devices and Biosensors, the Chinese University of Hong Kong, HKSAR, China, Jun. 1-3, 2008, p. 235-238.

Guo, Jing-Yi et al., "Evaluation of Sonomyography (SMG) for Control Compared with Electromyography (EMG) in a Discrete Target Tracking Task", 31st Annual International Conference of the IEEE EMBS, Minneapolis, Minnesota, USA, Sep. 2-6, 2009, p. 1549-1552.

* cited by examiner

ARTIFICIAL BODY PART CONTROL SYSTEM USING ULTRASONIC IMAGING

CROSS-REFERENCE TO RELATED APPLICATIONS

This application claims the benefit of U.S. Provisional Application No. 61/513,789, filed Aug. 1, 2011, entitled "Ultrasonic Prosthetic Controller," which is hereby incorporated by reference in its entirety. This disclosure relates in general, but not by way of limitation, to control of a prosthetic arm using an ultrasonic image analyzer amongst other things.

STATEMENT REGARDING FEDERALLY SPONSORED RESEARCH OR DEVELOPMENT

This invention was made with government support under grant number 0953652 awarded by the National Science Foundation. The government has certain rights in the invention.

DETAILED DESCRIPTION OF EMBODIMENTS

The ensuing description provides exemplary embodiment only, and is not intended to limit the scope, applicability or configuration of the disclosure. Rather, the ensuing description of the exemplary embodiment will provide those skilled in the art with an enabling description for implementing an exemplary embodiment. It being understood that various changes may be made in the function and arrangement of elements without departing from the essence and scope set forth in the appended claims.

I. Artificial Body Part Control System Using Ultrasonic Imaging

In ultrasonography, sound waves propagating through soft tissue are scattered by the tissue microstructure and reflected at interfaces between two tissue types with differing acoustic impedance. As a result, anatomical ultrasound images are characterized by the brightness (echogenicity) associated with the strength of the backscattered echoes, and the echo texture of image (echo texture or speckle) associated with the pattern of constructive and destructive interference as sound waves propagate through the tissue microstructure. Tissues are identifiable on an ultrasonic image because the echogenicity and echo texture are unique for different underlying tissue. Tissues may appear darker during a contractile event compared to the relaxed state. The artificial body part control system using ultrasonic imaging, according to one embodiment of the invention, uses image-processing to track the motion of target tissue groups based on the changes in echogenicity and speckle patterns in order to generate a control signal corresponding to movement or non-movement. The control system may determine tissue movement by comparing pixel intensity changes, Doppler shift or phase changes of the received ultrasound signals within a region of interest over time. Comparing such changes within a region of interest allows the control system to determine the nature of any intended tissue movements and render a control signal to an artificial joint.

According to one embodiment of the invention, the artificial body part control system may determine intended joint movements in a target limb by ultrasonically monitoring contractions in the muscles that are directly associated with controlling that joint from at least two-dimensional ultrasonic images. For example, the digits in a prosthetic hand may be controlled by monitoring the muscle contraction events in the forearm muscles in a transradial amputee with the appropriate forearm muscles intact. Therefore, among the multiple target locations for the artificial body part control system, the target location for some embodiments may be the muscles of the mid-anterior forearm to determine intended movements in the human hand.

Figure 1:
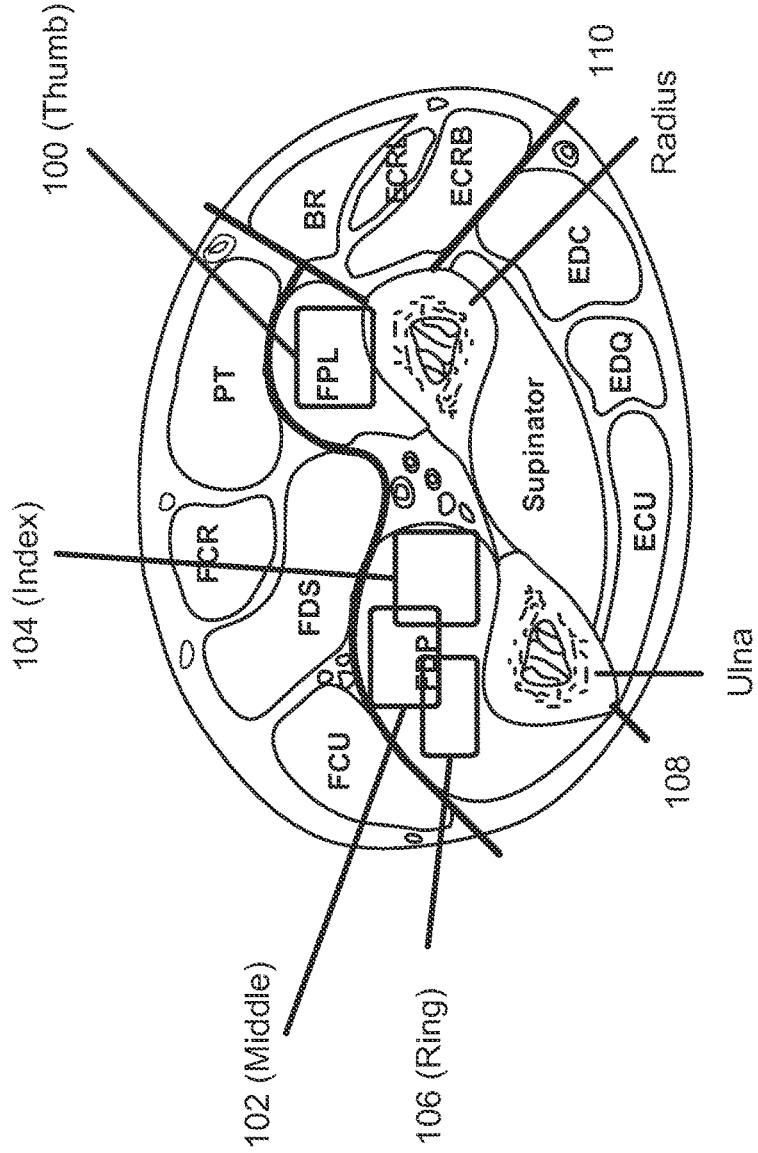
FIG. 1 shows examples of ultrasonic windows that may be employed in at least two-dimensional images generated by at least one ultrasonic transducer over a cross-section of the forearm.

FIG. 1 shows a cross-section of the muscles and nerves of the forearm that may be targeted by an ultrasonic transducer. Window 100 shows the area of the forearm that may control thumb movement, 102 shows the area that may control movement in the middle finger, 104 shows that may control the index finger, and 106 shows the area that may control the ring finger.

Figure 2:
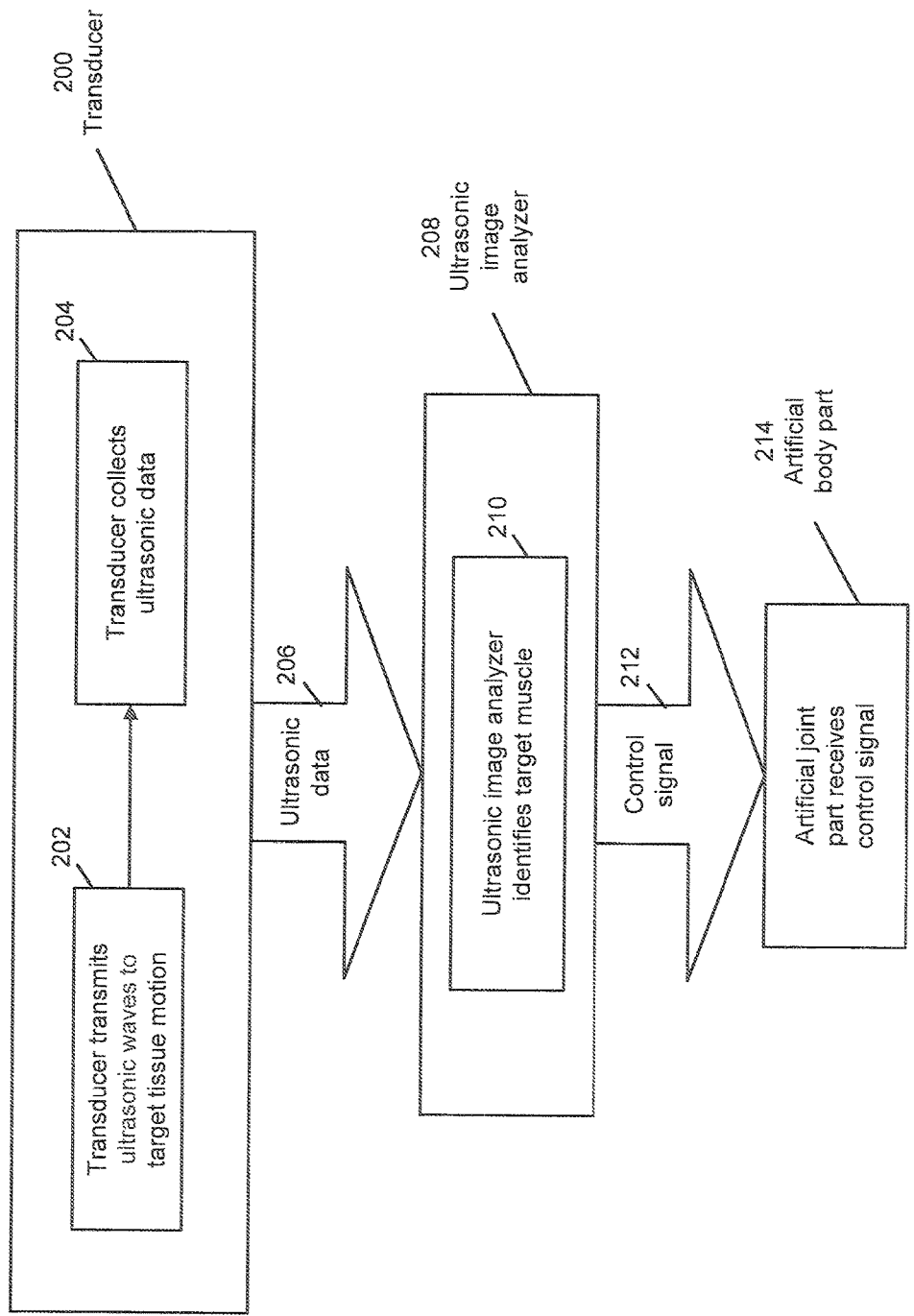
FIG. 2 shows a flow diagram of an ultrasonic imaging analyzer and artificial body part control system according to one embodiment of the invention.

FIG. 2 shows a flow diagram of an artificial body part control system for a prosthetic hand according to one embodiment of the invention. The ultrasonic transducer 200 may transmit ultrasonic waves to a tissue group of interest ("target tissue") at block 202. The target tissue may include muscles of the forearm. The ultrasonic transducer 200 may collect ultrasonic data in the form of at least two-dimensional images backscattered by the muscles at block 204. The ultrasonic image analyzer 208 may receive the ultrasonic data 206 from the transducer and may in real time determine the origin and magnitude of the muscle movement by detecting pixel intensity changes, Doppler shift or phase changes in the ultrasonic data at block 210. The ultrasonic image analyzer may communicate a control signal 212 to the prosthetic joint 214. In alternative embodiments, the movement of the artificial body part at block 214 may be fed back to the operator to implement haptic feedback control.

Figure 3:
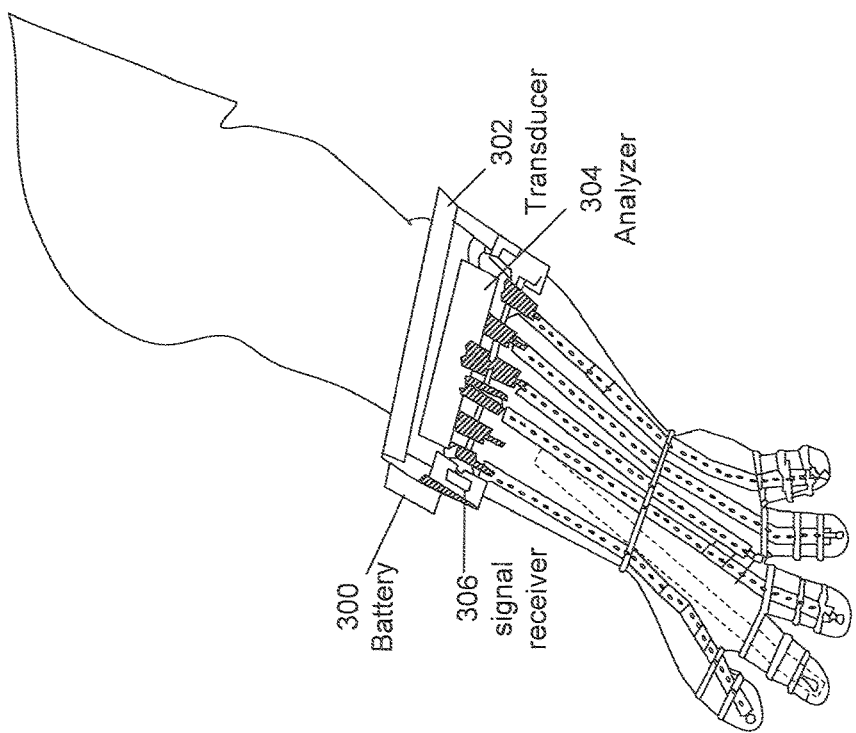
FIG. 3 is an illustration of an ultrasonic transducer cuff and transmitter attached to one artificial body part control system according to one embodiment of the invention.

FIG. 3 is an illustration of an ultrasonic transducer cuff and artificial body part control system, according to one embodiment of the invention. Battery pack 300 may be attached to the control system. In one embodiment of the invention, the ultrasonic transducer cuff 302 may be designed to wrap around the forearm limb where the transducer acquires ultrasonic data resulting from flexion of target muscle tissues. The transducer cuff may be designed to wrap around other limbs or body parts. Embodiments of the invention may utilize an ultrasonic transducer such as an Interson 7.5 MHz single-element motor-controlled ultrasonic transducer. An array of transducers may be employed on the ultrasonic cuff 302, permitting the acquisition of ultrasonic data from multiple dimensions. Various other formations of the transducer array may be implemented. In this embodiment, each transducer may be rotatable and placed in a socket that contains a locking mechanism that allows the user to lock the transducer at a desired angle. The transducer may send the acquired ultrasonic data to the ultrasonic image analyzer 304 for image analysis. In this embodiment, the ultrasonic analyzer 304 may contain a data storage device designed to store ultrasonic template data. Upon completion of image analysis, the ultrasonic image analyzer 304 may transmit a control signal to the microcontroller in the artificial body part 306;

II. Training the Ultrasonic Image Analyzer

Figure 4:
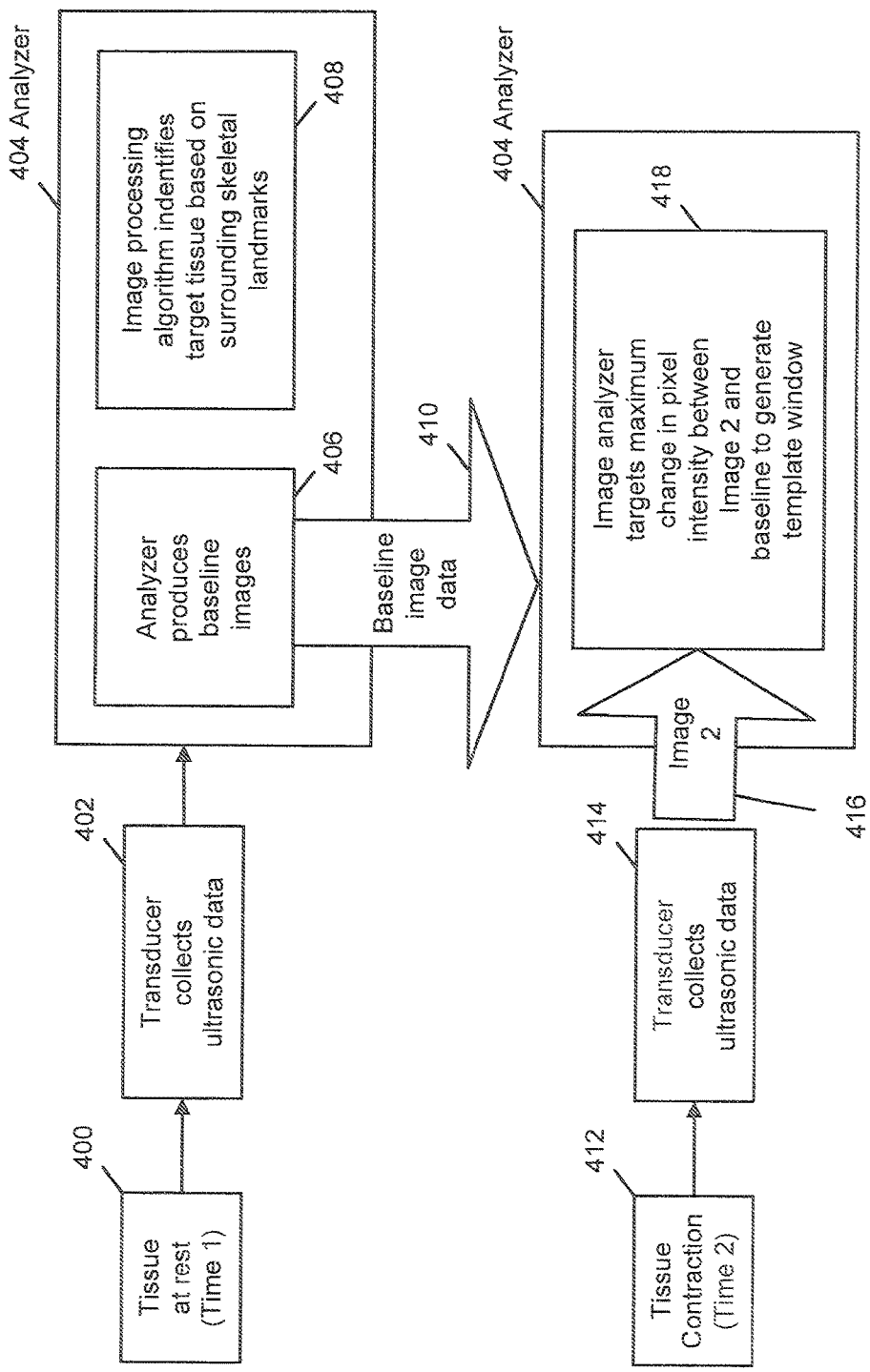
FIG. 4 shows a block diagram of a process for training an ultrasonic image analyzer to generate one template window.

The artificial body part control system training processes are provided according to one embodiment of the invention. In one embodiment of the invention, the analyzer may produce a control signal for an artificial body part, such as a prosthetic hand, by identifying the target tissue group in the forearm that corresponds to the intended joint movement in the prosthetic hand. The analyzer may continuously generate control signals by ultrasonically monitoring the subsequent movements in the target tissues. The ultrasonic analyzer determines or identifies target tissue groups on an ultrasound image by selecting template windows that include the region where the target tissue is located ("region of interest"). FIG. 4 shows a block diagram of a process for training an ultrasonic image analyzer to select a template window for the forearm muscle tissue movement that produces a finger flexion. These template windows may be specific to each individual user.

At time 1 at block 400, the tissue is at rest and not moving. The transducer may collect the ultrasonic data at block 402, and may transmit the data to the analyzer 404. At block 406, the analyzer may produce a baseline ultrasonic image 410 of the tissue at rest and this image may be saved. The analyzer may identify the target tissue that produced the baseline image by identifying surrounding skeletal landmarks at block 408.

The analyzer may identify skeletal landmarks by executing an image-processing algorithm that may allow the analyzer to recognize a bone's characteristic pattern of hyperechogenicity followed by a hypoechoeic shadow. FIG. 1 shows the muscles of the forearm relative to the radius bone 110 and the ulna bone 108. The analyzer may determine the location of the radius 110 and ulna 108 by recognizing the bones' characteristic pattern of echogenicity. Once these bones are identified, the analyzer may locate the approximate position of the target tissues, such as the muscle tissues that flex the digits 100, 102, 104, 106.

At time 2, user contracts the target tissue to generate an ultrasonic image at block 412. The transducer may collect the ultrasonic data of the tissue contraction at block 414 and may transmit this data 416 to the analyzer 404.

The analyzer 404 may compare the baseline image data 410 to image 2 416. The user may have to contract the same tissue multiple times to allow the ultrasonic analyzer to collect the data. At block 418, the image-processing algorithm may target the area on image 2 416 that showed the greatest pixel intensity change in comparison to the corresponding baseline image. The area with the greatest pixel intensity changes may be selected by the analyzer 404 to be the template window containing the region of interest at block 418. As an alternative to pixel intensity, Doppler shift or phase changes may be monitored.

Figure 5:
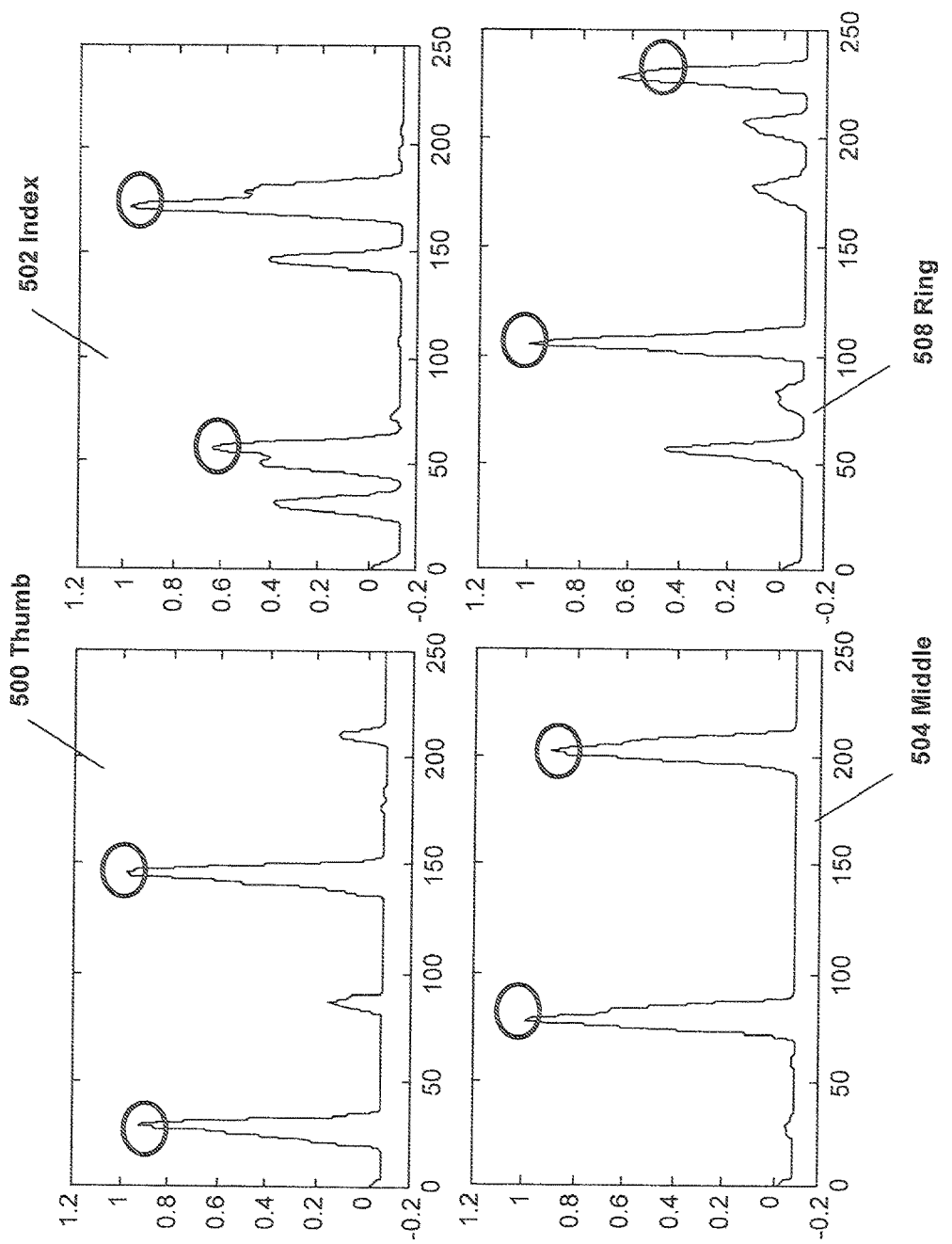
FIG. 5 shows characteristic movement waveforms derived from ultrasound data generated within the template windows graphed in terms of pixel intensity over time.

In one embodiment of the invention, after selection of the template window, the transducer may continuously collect at least two-dimensional images of the target tissue flexion. The analyzer may use the collected data to plot characteristic movement waveforms of the tissue flexion in terms of pixel intensity changes over time. FIG. 5 shows examples of waveforms or signals generated by the analyzer by monitoring areas within the template windows. The spikes in the graphs reflect pixel intensity changes as the thumb 500, index 502, middle 504, and ring finger 508, flexes over time. The analyzer may identify template windows to be areas generating the largest and most well-defined waveforms to reflect larger pixel intensity changes, and therefore, the greatest change from baseline.

Figure 6:
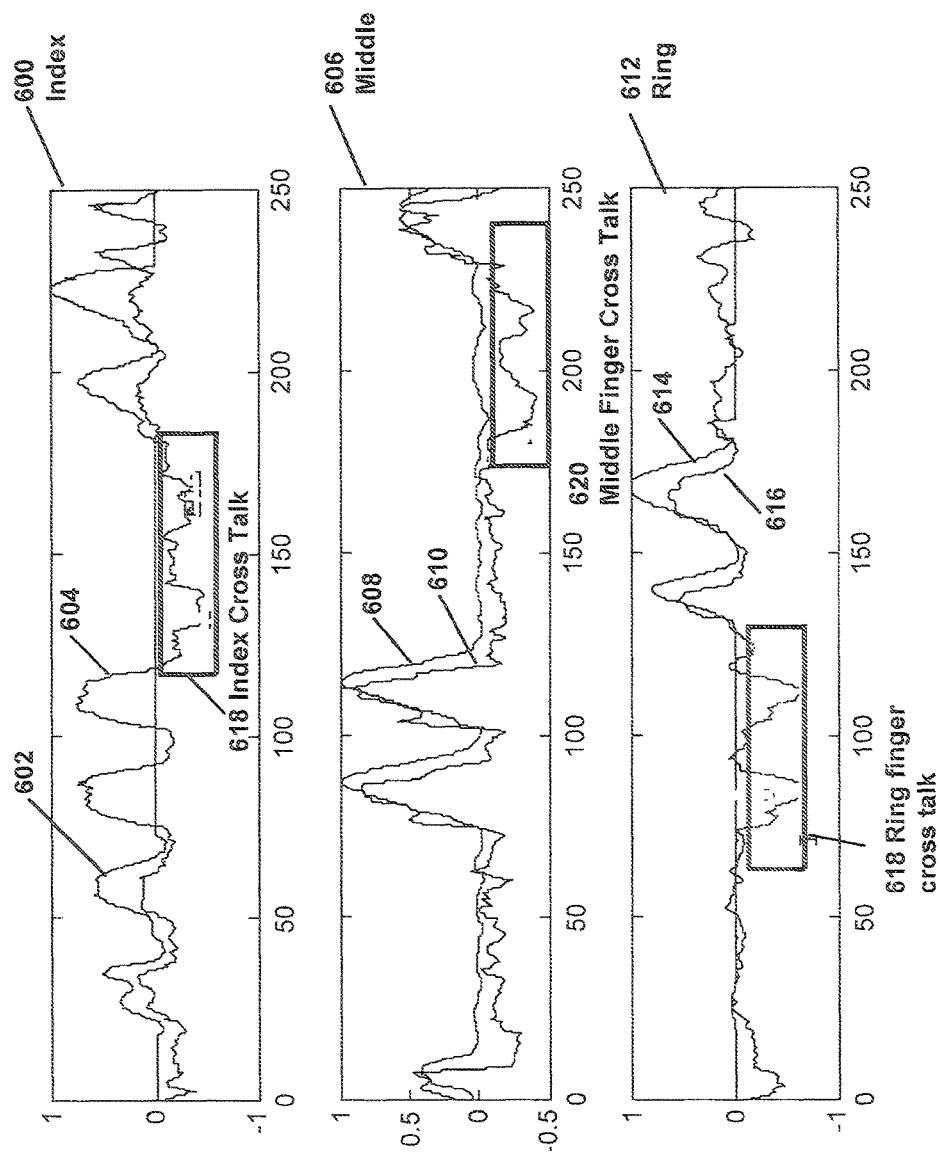
FIG. 6 shows examples of sum of the difference waveforms generated within a template window in comparison to the waveforms generated outside of the template windows.

The analyzer may produce control signals for continuous movement of a target tissue group by calculating the sum of the difference of pixel intensity changes for different frames within a template window that reflect ongoing tissue movement. FIG. 6 show examples of sum of the difference waveforms calculated by taking the sum of the difference of the pixel intensity changes of every frame within a template window. In one embodiment of the invention, the sum of the differences is calculated by subtracting pixels between a reference frame and a target frame within template window, followed by the aggregation of absolute differences within the window. For example, the analyzer may identify the tissue movement within the template window over time by calculating the sum of the difference of the pixel intensity changes between frame 1 (at time 1) and frame 0 (at baseline), then frame 2 (at time 2) and frame 1. The analyzer may also be configured to calculate the pixel intensity changes between frame 1 and frame 0, frame 2 and frame 0 and so on, amongst others.

The sum of absolute difference may be expressed as:

$$\epsilon_{m,n} = \sum_{i=1}^{k} \sum_{j=1}^{l} |X_{i,j} - Y_{i+m,j+n}|$$

where X and Y are pixel intensities in two different frames at pixel locations indicated by the subscripts; k and l correspond to the size of the window over which the sum of difference is computed; and $\epsilon_{m,n}$ is the sum of the difference of a set of frames.

FIG. 6 compares the sum of the differences waveforms generated within template windows selected by the analyzer with the sum of the difference waveforms generated by one entire ultrasound image acquired by the transducer. For example, 600 compares the sum of the difference waveform generated by calculating the pixel intensity changes of frames within a template window for the muscle flexing the index finger 602, with a sum of the difference waveform generated from the overall ultrasound image acquired by a transducer 604. As the window used to generate 604 is not targeted to the specific region of interest, it created cross-talk 618 as signals generated by other concurrent muscle movements are detected. 606 compares the sum of the difference waveform generated within a template window specifically targeting the middle finger 608 and a sum of the difference waveform produced by the overall ultrasonic image 610 which created cross-talk 620. And 612 compares the sum of the difference waveform generated by calculating the pixel intensity changes within a template window for the ring finger 614 and a sum of the difference waveform generated by calculating the pixel intensity changes of the entire ultrasound image 616 which created cross-talk 618. The presence of significant cross-talk may distort the subsequent control signal.

III. Using the Ultrasonic Artificial Body Part Controller

Figure 7:
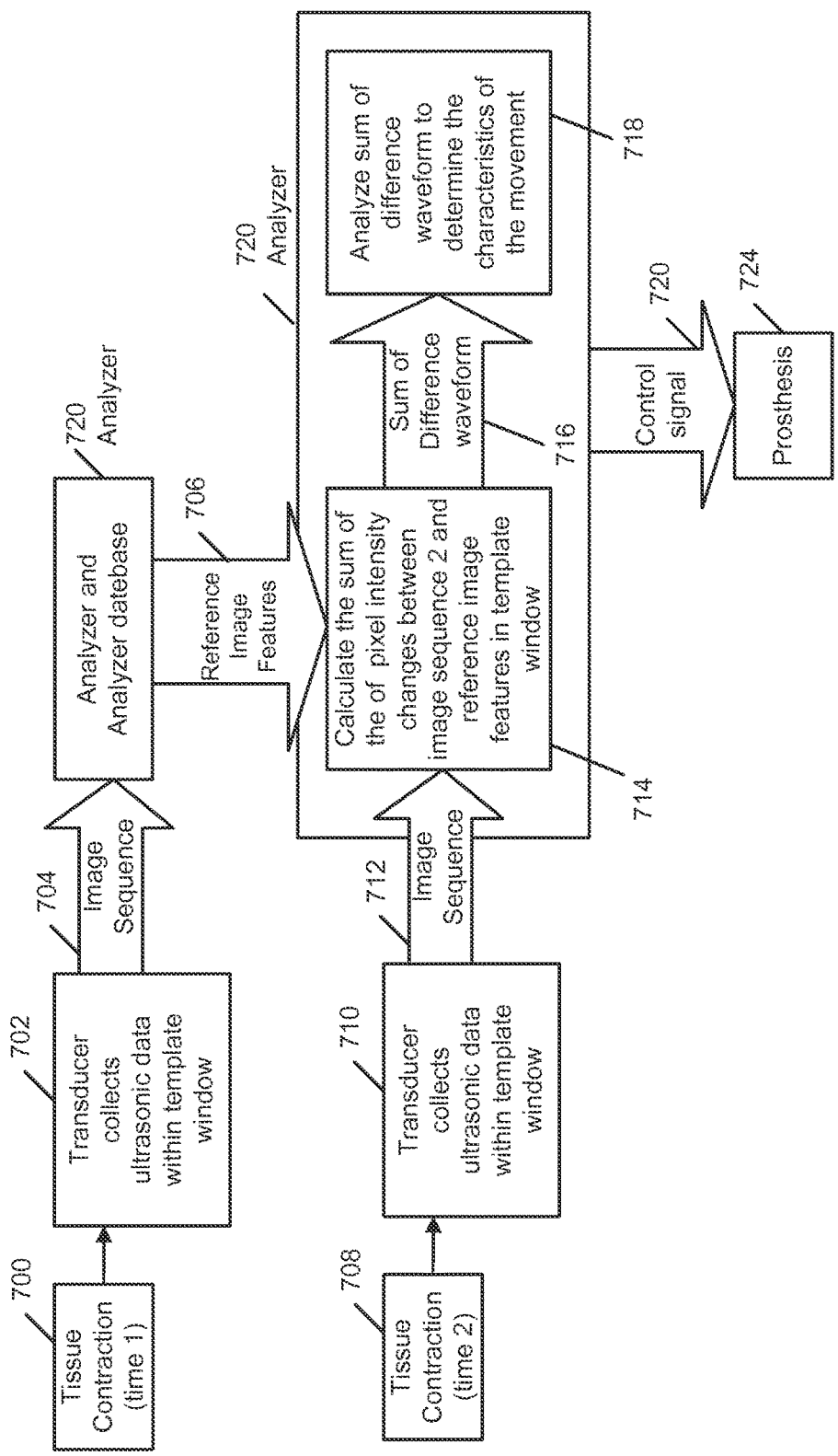
FIG. 7 is a flow diagram showing the operation of the artificial body part control system according to one embodiment of the invention.

FIG. 7 shows a flow diagram of the ultrasonic artificial body part controller in use after training. At block 700 a tissue contracts. The transducer may collect the ultrasonic data of the tissue contraction in the form of at least two-dimensional images within an already selected template window at block 702 to generated image sequence 1 704. The analyzer 720 may store the image sequence 1 data 704 within its database as reference image features. At time 2, the same tissue contracts again at block 708. The transducer may collect the ultrasonic data at block 710 and may transmit the image sequence 2 712 to the analyzer 720. At block 714, the analyzer 720 may execute in real time an algorithm that calculates the sum of the difference change of the pixel intensity between image sequence 2 712 and reference image features 706. The analyzer 720 may generate a sum of the difference waveform 716. Image sequence 2 712 may also be stored in the analyzer's database 720 and may be used to compare pixel intensity changes of subsequent frames. The analyzer 720 may also analyze the sum of the difference waveform 716 to determine the characteristics of the tissue movement, such as intensity, rate, and duration at block 718. The analyzer 720 may transmit a control signal 722 to an artificial body part 724.

Figure 8:
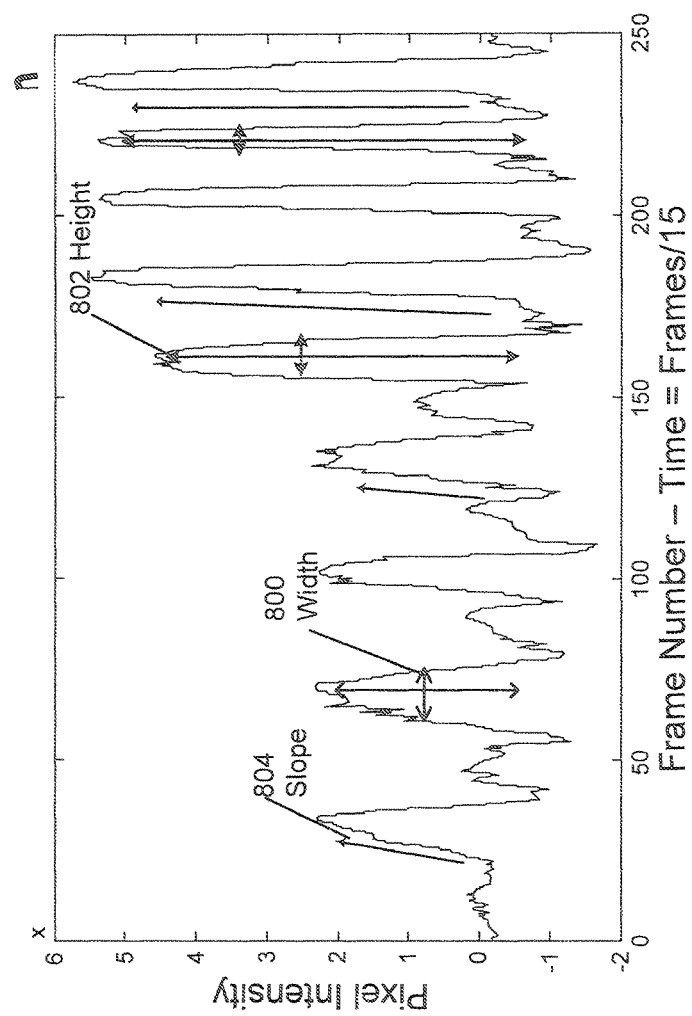
FIG. 8 shows a thumb contraction characteristic movement waveform derived from ultrasound data plotted in terms of pixel intensity over time.

FIG. 8 shows a sum of the difference waveform of a thumb contraction, which would be used by the ultrasonic image analyzer to determine the characteristics of the thumb tissue flexing the thumb. As illustrated at 500 in FIG. 5, according to one embodiment of the invention. Embodiments may relate the degree (amount) of tissue contraction to the height of the waveform 802. Embodiments may relate the duration of tissue contraction with the width at ½ height of the waveform 800. Embodiments may relate the rate of tissue contraction with the slope 804, taken between 20% and 80% of wave height.

Another method that the analyzer may use to estimate tissue contraction velocities is by using a process called vector tissue Doppler imaging. This process estimates tissue motion in two or more independent directions using multiple transmitters and receivers oriented in different directions. The vector Doppler method combines the multiple velocity estimates producing a velocity vector with magnitude and direction. An array of transducers may be employed and split into a set of transmit apertures and a set of receiver apertures that steer and receive the Doppler beams. The magnitude of the resultant velocity vector can then be obtained from the individual velocity components as:

$$v = \frac{c}{4f_t}\sqrt{\left(\frac{f_1+f_2}{\cos\beta}\right)^2 + \left(\frac{f_1-f_2}{\sin\beta}\right)^2}$$

where $\beta$ is the beam steering angle, $f_1$ and $f_2$ are the two received frequency components, c is the speed of sound, and $f_t$ is the transmitted ultrasound frequency. This method can be applied to detect muscle contraction velocities, as well as tendon velocities. Alternatively, phase changes may be monitored.

Figure 9:
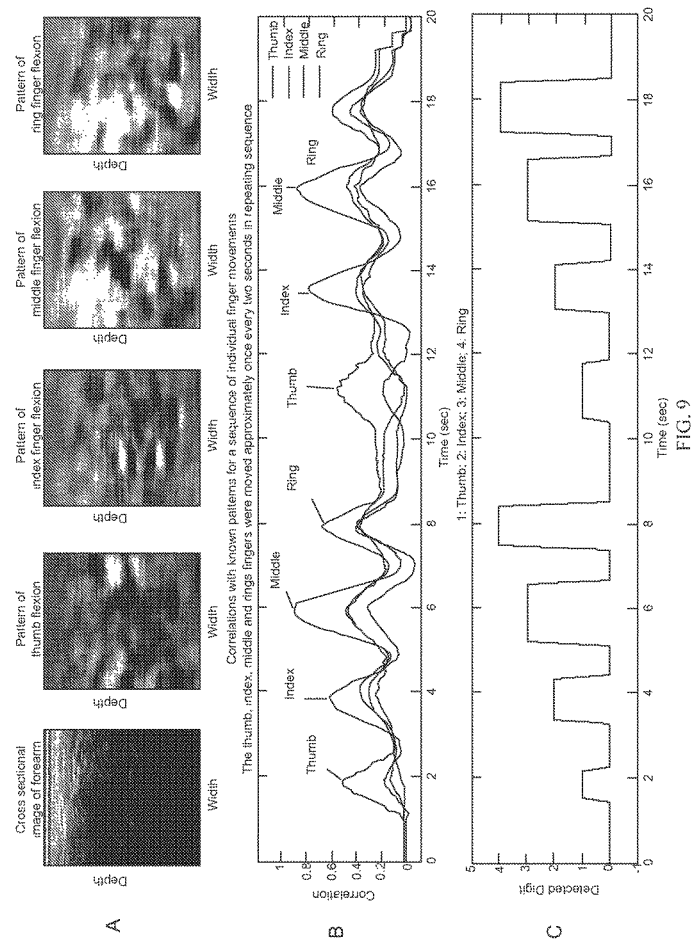
FIG. 9 shows images and waveforms associated with a characteristic pattern embodiment.

In another method, the analyzer may identify patterns of tissue movement based on changes in ultrasound echo intensities (echogenicity) over time. FIG. 9 is an example implementation of this method. The top left panel in row A of FIG. 9 shows a cross sectional image of the forearm, while the remaining panels on the top row A show patterns of activity for different individual finger movement determined during a training session and entered as reference image ultrasound data into a database. Subsequent patterns may then be utilized to decode the intended movement in real time. The waveforms in the middle row B were obtained during two repetitions of a sequence of thumb, index, middle and ring finger movements, approximately once every two seconds, with a pause in between. The waveforms show the correlations between the current pattern of movement and the best match with patterns from the database of reference image ultrasound data corresponding to individual finger movements. The best match can then be decoded from these waveforms to detect the intended digit movement, as shown in the waveform in the bottom row C. The thumb, index, middle and ring finger movements have been correctly decoded in real time.

IV. Background Information and Aid to Explain the Present Embodiments

In this specification, "a" and "an" and similar phrases are to be interpreted as "at least one" and "one or more." References to "an" embodiment in this disclosure are not necessarily to the same embodiment.

According to some embodiments, an ultrasound video may be created using an ultrasound-imaging program such as SeeMore or the like. SeeMore may be obtained from Interson Corporation of Pleasanton, Calif. The ultrasound video may be imported via an import mechanism such is available from MATLAB. MatLab is available from The MathWorks, Inc. of Natick, Mass. The imported data may be processed.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e hardware with a biological element) or a combination thereof, all of which are behaviorally equivalent. For example, modules may be implemented using computer hardware in combination with software routine(s) written in a computer language (such as C, C, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described exemplary embodiments. In particular, it should be noted that, for example purposes, the above explanation has focused on the example of using an ultrasonic controller for prosthetic control. However, one skilled in the art will recognize that embodiments of the invention could be used to control other types of artificial limbs, such as an iron lung or a robotic armor. In addition to prosthetic control, this technology may also be used in rehabilitation to quantify muscle dynamics associated with complex functional tasks.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A control system, comprising:
   at least one ultrasonic transducer configured to produce at least a temporal sequence of two-dimensional image ultrasound data of tissue associated with controlling individual movement of a plurality of artificial body parts; and
   an image analyzer coupled to the at least one ultrasonic transducer configured to:
      generate, in real time, output signals adapted to control individual movement of one or more of the plurality of artificial body parts, by:
         detecting, by executing an image-processing algorithm, a characteristic pattern of echogenicity and a characteristic pattern of echo texture, wherein the characteristic pattern of echogenicity and the characteristic pattern of echo texture indicate an origin and a magnitude of movement of a plurality of muscle tissues and a plurality of bones,
         generating, based on the detected characteristic pattern of echogenicity and the detected characteristic pattern of echo texture, image features corresponding to an intended activity comprising one or more movements of the one or more of the plurality of artificial body parts,
         comparing the image features to each of a plurality of reference image features associated with the movement of the plurality of muscle tissues involved with the intended activity,
         determining, based on the comparison, a best match for the intended activity, and
         generating, based on the best match, the output signals adapted to control individual movement of the one or more of the plurality of artificial body parts.

2. The control system of claim 1, wherein detecting, by executing the image-processing algorithm, the characteristic pattern of echogenicity and the characteristic pattern of echo texture comprises identifying movement of the plurality of muscle tissues by calculating pixel intensity changes between at least two ultrasonic image frames over time.

3. The control system of claim 2, wherein the image processing algorithm determines the characteristic pattern of echogenicity and the characteristic pattern of echo texture by analyzing differences in pixel intensity between at least two ultrasound image frames over time.

4. The control system of claim 2, wherein determining, based on the comparison, the best match for the intended activity comprises identifying the intended activity by finding a closest match to the characteristic pattern of echogenicity and the characteristic pattern of echo texture and corresponding image features associated with the intended activity from a database of characteristic patterns of echogenicity and echo texture and corresponding image features associated with different movements.

5. The control system of claim 1, wherein the characteristic pattern of echogenicity comprises a pattern of brightness associated with a strength of backscattered echoes.

6. The control system of claim 1, wherein the characteristic pattern of echo texture comprises a pattern of constructive and destructive interference as sound waves propagate through tissue microstructure.

7. The control system of claim 1, wherein detecting, by executing the image-processing algorithm, the characteristic pattern of echogenicity and the characteristic pattern of echo texture comprises:
   storing a first ultrasonic image frame received at a first time in a database;
   storing a second ultrasonic image frame received at a second time in the database;
   determining a pattern of dissimilarity between the pixel intensity between the second ultrasonic image frame and the first ultrasonic image frame; and
   generating one or more dissimilarity waveforms that indicate the changes in pixel intensities over time.

8. The control system of claim 7, wherein generating, based on the detected characteristic pattern of echogenicity and the detected characteristic pattern of echo texture, image features corresponding to the intended activity comprises analyzing the one or more dissimilarity waveforms to determine the intended activity.

9. The control system of claim 8, wherein the image features corresponding to the intended activity comprise one or more of an intensity of movement of the plurality of muscle tissues and the plurality of bones, a rate of movement of the plurality of muscle tissues and the plurality of bones, or a duration of movement of the plurality of muscle tissues and the plurality of bones.

10. The control system of claim 9, wherein analyzing the one or more dissimilarity waveforms to determine the intended activity comprises:
    determining a height of the one or more dissimilarity waveforms as the intensity of movement of the plurality of muscle tissues and the plurality of bones;
    determining the width of the one or more dissimilarity waveforms as the duration of movement of the plurality of muscle tissues and the plurality of bones; and determining the slope of the one or more dissimilarity waveforms as the rate of movement of the plurality of muscle tissues and the plurality of bones.

11. The control system of claim 1, wherein determining, based on the comparison, a best match for the intended activity comprises determining a correlation between the characteristic pattern of echogenicity and the characteristic pattern of echo texture and corresponding image features produced by the movement of the plurality of muscle tissues and the plurality of bones from a database of associated different movements.

12. A control system, comprising:
at least one ultrasonic transducer configured to produce at least a temporal sequence of two-dimensional image ultrasound data of tissue associated with controlling individual movement of a plurality of artificial body parts; and
an image analyzer coupled to the at least one ultrasonic transducer configured to:
generate, in real time, output signals adapted to control individual movement of one or more of the plurality of artificial body parts, by:
detecting, by executing an image-processing algorithm, a characteristic pattern of echogenicity and a characteristic pattern of echo texture, wherein the characteristic pattern of echogenicity and the characteristic pattern of echo texture indicate an origin and a magnitude of movement of a plurality of muscle tissues and a plurality of bones,
generating, based on the detected characteristic pattern of echogenicity and the detected characteristic pattern of echo texture, image features corresponding to an intended activity comprising one or more movements of the one or more of the plurality of artificial body parts,
wherein the image features comprise one or more of an intensity of movement of the plurality of muscle tissues and the plurality of bones, a rate of movement of the plurality of muscle tissues and the plurality of bones, or a duration of movement of the plurality of muscle tissues and the plurality of bones,
comparing the image features to each of a plurality of reference image features associated with the movement of the plurality of muscle tissues and the plurality of bones involved with the intended activity,
determining, based on the comparison, a best match for the intended activity, and
generating, based on the best match, the output signals adapted to control individual movement of the one or more of the plurality of artificial body parts.

13. The control system of claim 12, wherein detecting, by executing the image-processing algorithm, the characteristic pattern of echogenicity and the characteristic pattern of echo texture comprises identifying movement of the plurality of muscle tissues and the plurality of the plurality of bones by calculating pixel intensity changes between at least two ultrasonic image frames over time.

14. The control system of claim 12, wherein the image processing algorithm determines the characteristic pattern of echogenicity and the characteristic pattern of echo texture by analyzing differences in pixel intensity between at least two ultrasound image frames over time.

15. The control system of claim 12, wherein determining, based on the comparison, the best match for the intended activity comprises identifying the intended activity by finding a closest match to the characteristic pattern of echogenicity and the characteristic pattern of echo texture and corresponding image features associated with the intended activity from a database of characteristic patterns of echogenicity and echo texture and corresponding image features associated with different movements.

16. The control system of claim 12, wherein the characteristic pattern of echogenicity comprises a pattern of brightness associated with a strength of backscattered echoes.

17. The control system of claim 12, wherein the characteristic pattern of echo texture comprises a pattern of constructive and destructive interference as sound waves propagate through tissue microstructure.

18. The control system of claim 12, wherein detecting, by executing the image-processing algorithm, the characteristic pattern of echogenicity and the characteristic pattern of echo texture comprises:
storing a first ultrasonic image frame received at a first time in a database;
storing a second ultrasonic image frame received at a second time in the database;
determining a pattern of dissimilarity between the pixel intensity between the second ultrasonic image frame and the first ultrasonic image frame; and
generating one or more dissimilarity waveforms that indicate the changes in pixel intensities over time.

19. The control system of claim 18, wherein generating, based on the detected characteristic pattern of echogenicity and the detected characteristic pattern of echo texture, image features corresponding to the intended activity comprises analyzing the one or more dissimilarity waveforms to determine the intended activity.

20. The control system of claim 19, wherein analyzing the one or more dissimilarity waveforms to determine the intended activity comprises:
determining a height of the one or more dissimilarity waveforms as the intensity of movement of the plurality of muscle tissues;
determining the width of the one or more dissimilarity waveforms as the duration of movement of the plurality of muscle tissues; and
determining the slope of the one or more dissimilarity waveforms as the rate of movement of the plurality of muscle tissues.

21. The control system of claim 12, wherein determining, based on the comparison, a best match for the intended activity comprises determining a correlation between the characteristic pattern of echogenicity and the characteristic pattern of echo texture and corresponding image features produced by the movement of the plurality of muscle tissues and the plurality of bones from a database of associated different movements.

22. A method, comprising:
producing at least a temporal sequence of two-dimensional image ultrasound data of tissue associated with controlling individual movement of a plurality of artificial body parts;
detecting a characteristic pattern of echogenicity and a characteristic pattern of echo texture, wherein the characteristic pattern of echogenicity and the characteristic pattern of echo texture indicate an origin and a magnitude of movement of a plurality of muscle tissues,
generating, based on the detected characteristic pattern of echogenicity and the detected characteristic pattern of echo texture, image features corresponding to an intended activity comprising one or more movements of one or more of the plurality of artificial body parts, wherein the image features corresponding to the intended activity comprise one or more of an intensity of movement of the plurality of muscle tissues, a rate of movement of the plurality of muscle tissues, or a duration of movement of the plurality of muscle tissues, comparing the image features to each of a plurality of reference image features associated with the movement of the plurality of muscle tissues involved with the intended activity, determining, based on the comparison, a best match for the intended activity, and generating in real time, based on the best match, output signals adapted to control individual movement of the one or more of the plurality of artificial body parts.

23. The method of claim 22, wherein detecting, by executing the image-processing algorithm, the characteristic pattern of echogenicity and the characteristic pattern of echo texture comprises:

storing a first ultrasonic image frame received at a first time in a database;

storing a second ultrasonic image frame received at a second time in the database;

determining a pattern of dissimilarity between the pixel intensity between the second ultrasonic image frame and the first ultrasonic image frame; and generating one or more dissimilarity waveforms that indicate the changes in pixel intensities over time.

24. The method of claim 22, wherein generating, based on the detected characteristic pattern of echogenicity and the detected characteristic pattern of echo texture, image features corresponding to the intended activity comprises analyzing the one or more dissimilarity waveforms to determine the intended activity.

25. The method of claim 22, wherein analyzing the dissimilarity waveform to determine the intended activity comprises:

determining a height of the one or more dissimilarity waveforms as the intensity of movement of the plurality of muscle tissues;

determining the width of the one or more dissimilarity waveforms as the duration of movement of the plurality of muscle tissues; and determining the slope of the one or more dissimilarity waveforms as the rate of movement of the plurality of muscle tissues.

* * * * *